United States Patent
Niedermeyer

(10) Patent No.: US 10,190,253 B2
(45) Date of Patent: Jan. 29, 2019

(54) NANOPARTICLE TREATED FABRICS, FIBERS, FILAMENTS, AND YARNS AND RELATED METHODS

(71) Applicant: ATTOSTAT, INC., Salt Lake City, UT (US)

(72) Inventor: William Harold Niedermeyer, West Jordan, UT (US)

(73) Assignee: ATTOSTAT, INC, Salt Lake City, UT (US)

( * ) Notice: Subject to any disclaimer, the term of this patent is extended or adjusted under 35 U.S.C. 154(b) by 332 days.

(21) Appl. No.: 14/861,375

(22) Filed: Sep. 22, 2015

(65) Prior Publication Data
US 2016/0083901 A1   Mar. 24, 2016

Related U.S. Application Data

(60) Provisional application No. 62/054,182, filed on Sep. 23, 2014.

(51) Int. Cl.
*D06M 23/02* (2006.01)
*H01B 1/02* (2006.01)
(Continued)

(52) U.S. Cl.
CPC .............. *D06M 23/02* (2013.01); *A01N 59/16* (2013.01); *D06M 11/83* (2013.01); *G02B 5/122* (2013.01);
(Continued)

(58) Field of Classification Search
CPC ........ D06M 11/83; D06M 23/02; A01N 59/16
(Continued)

(56) References Cited

U.S. PATENT DOCUMENTS

| 4,515,740 A | 5/1985 | Schuttenberg et al. |
| 5,227,608 A | 7/1993 | Yoshida |

(Continued)

FOREIGN PATENT DOCUMENTS

| CN | 102120619 | 7/2011 |
| CN | 103891558 | 7/2014 |

(Continued)

OTHER PUBLICATIONS

Agnihotri, Shekar, et al., "Immobilized silver nanoparticles enhance contact killing and show highest efficacy: elucidation of the mechanism of bacterial action of silver," Nanoscale, 2013. published Jan. 3, 2013. (Year: 2013).*

(Continued)

*Primary Examiner* — Matthew D Matzek
(74) *Attorney, Agent, or Firm* — Workman Nydegger

(57) ABSTRACT

Nanoparticle treated fibrous articles, such as fabrics, fibers, filaments, or yarns, include a plurality of exposed, nonionic metal nanoparticles non-covalently affixed thereto. Metal nanoparticles, particularly spherical-shaped metal nanoparticles which have solid cores, can be strongly affixed to fibrous articles without covalently bonds and/or without being encapsulated within a polymer or adhesive. Spherical metal nanoparticles appear to adhere to fibrous articles by Van der Waals forces. Because they are nonionic, spherical nanoparticles are not easily removed by solvents, water, surfactants, and soaps and remain after several washings, sometimes up to 50 or more washings. Nonetheless, they readily detach from fibrous articles when contacted by microbes and then kill or denature the microbes. Coral-shaped nanoparticles can be used in conjunction with spherical nanoparticles to assist in affixing the spherical nanoparticles and/or by themselves or in combination with spherical particles to kill or denature microbes.

20 Claims, 8 Drawing Sheets

(51) Int. Cl.

| | | |
|---|---|---|
| *A01N 59/16* | (2006.01) | |
| *D06M 11/83* | (2006.01) | |
| *G21F 1/12* | (2006.01) | |
| *G02B 5/122* | (2006.01) | |
| *G02B 5/22* | (2006.01) | |
| *G02B 5/28* | (2006.01) | |
| *G02B 27/10* | (2006.01) | |
| *G02B 27/14* | (2006.01) | |

(52) U.S. Cl.
CPC ............... *G02B 5/22* (2013.01); *G02B 5/28* (2013.01); *G02B 27/1006* (2013.01); *G02B 27/141* (2013.01); *G21F 1/125* (2013.01); *H01B 1/02* (2013.01)

(58) Field of Classification Search
USPC ...... 442/123; 427/180, 434.6; 977/773, 775, 977/777
See application file for complete search history.

(56) References Cited

U.S. PATENT DOCUMENTS

| | | | |
|---|---|---|---|
| 5,390,864 | A | 2/1995 | Alexander |
| 5,585,020 | A | 12/1996 | Becker et al. |
| 6,509,070 | B1 | 1/2003 | Voevodin et al. |
| 7,014,737 | B2 | 3/2006 | Harutyunyan et al. |
| 7,371,457 | B2 | 5/2008 | Oldenburg et al. |
| 7,374,730 | B2 | 5/2008 | Simard et al. |
| 7,384,560 | B2 | 6/2008 | Martens et al. |
| 7,509,993 | B1 | 3/2009 | Turng et al. |
| 7,553,801 | B2 | 6/2009 | Alexander et al. |
| 7,662,731 | B2 | 2/2010 | Itoh et al. |
| 7,682,970 | B2 | 3/2010 | Grigoropoulos et al. |
| 7,700,032 | B1 | 4/2010 | Lu et al. |
| 7,884,160 | B2 | 2/2011 | Wang et al. |
| 7,985,367 | B2 | 7/2011 | Hiromatsu et al. |
| 8,685,293 | B1 | 4/2014 | Coppa et al. |
| 2001/0031564 | A1 | 10/2001 | Suzuki et al. |
| 2003/0086859 | A1 | 5/2003 | Kawakami et al. |
| 2003/0102099 | A1 | 6/2003 | Yadav et al. |
| 2004/0214001 | A1 | 10/2004 | Oldenburg et al. |
| 2006/0142853 | A1 | 6/2006 | Wang et al. |
| 2007/0287202 | A1 | 12/2007 | Maehashi et al. |
| 2008/0035682 | A1 | 2/2008 | Coffey et al. |
| 2008/0161631 | A1 | 7/2008 | Axtell et al. |
| 2008/0263940 | A1 | 10/2008 | Parish et al. |
| 2008/0292673 | A1 | 11/2008 | Crudden |
| 2009/0000186 | A1 | 1/2009 | Sanders et al. |
| 2009/0246530 | A1 | 10/2009 | Murakami et al. |
| 2010/0040655 | A1 | 2/2010 | Ren et al. |
| 2010/0050872 | A1 | 3/2010 | Lee |
| 2010/0068299 | A1 | 3/2010 | van der Krieken et al. |
| 2010/0072645 | A1 | 3/2010 | Hiromatsu et al. |
| 2010/0180413 | A1* | 7/2010 | Jeong ............... A01N 59/16 28/100 |
| 2010/0183739 | A1 | 7/2010 | Newman |
| 2010/0187091 | A1 | 7/2010 | Pierce et al. |
| 2010/0196192 | A1 | 8/2010 | Liu et al. |
| 2011/0039078 | A1 | 2/2011 | Brennan Fournet et al. |
| 2011/0052460 | A1 | 3/2011 | Coffey et al. |
| 2011/0193025 | A1 | 8/2011 | Ichikawa et al. |
| 2011/0197369 | A1* | 8/2011 | Hinestroza ......... D06M 10/025 8/115.6 |
| 2011/0228890 | A1 | 9/2011 | Dean et al. |
| 2011/0244056 | A1 | 10/2011 | Santra |
| 2012/0088066 | A1 | 4/2012 | Aytug et al. |
| 2012/0136164 | A1 | 5/2012 | Ying et al. |
| 2012/0138862 | A1 | 6/2012 | Hogan |
| 2012/0164073 | A1 | 6/2012 | Xu et al. |
| 2012/0174472 | A1 | 7/2012 | Mills |
| 2012/0301531 | A1 | 11/2012 | Uhlmann et al. |
| 2013/0001833 | A1* | 1/2013 | Niedermeyer ......... B82Y 40/00 264/400 |
| 2013/0203849 | A1* | 8/2013 | Ben Yehuda ........... A23B 4/20 514/557 |
| 2013/0334104 | A1* | 12/2013 | Halas ..................... B01D 3/02 208/348 |
| 2014/0274830 | A1 | 9/2014 | Pol et al. |
| 2014/0288194 | A1 | 9/2014 | Niedermeyer |
| 2016/0144350 | A1* | 5/2016 | Aizenberg ............. B01J 35/10 502/159 |

FOREIGN PATENT DOCUMENTS

| | | |
|---|---|---|
| CN | 104014811 | 9/2014 |
| KR | 20060021749 | 3/2006 |
| WO | WO2013141879 | 9/2013 |

OTHER PUBLICATIONS

U.S. Appl. No. 13/175,708, filed Jul. 1, 2011, Final Office Action dated Mar. 28, 2016.
International Search Report for PCT App. No. PCT/US2012/044907 dated Jan. 31, 2013.
U.S. Appl. No. 14/861,318, filed Sep. 22, 2015, Office Action dated Apr. 25, 2016.
U.S. Appl. No. 14/861,318, filed Sep. 22, 2015, Notice of Allowance dated May 20, 2016.
U.S. Appl. No. 14/861,318, filed Sep. 22, 2015, Corrected Notice of Allowance dated Jun. 15, 2016.
U.S. Appl. No. 15/088,863, filed Apr. 1, 2016, Tarbet et al.
U.S. Appl. No. 15/098,071, filed Apr. 13, 2016, Tarrbet et al.
U.S. Appl. No. 14/861,243, filed Sep. 22, 2015, Final Office Action dated Jul. 26, 2016.
Santos et al., "Enhancemetn of antibiotic effect via gold:silver-alloy nanoparticles", J. Nanopart Res (2012) 14:859, pp. 1-8.
U.S. Appl. No. 14/864,243, filed Sep. 22, 2015, Office Action dated Nov. 2, 2016.
Prabhu et al., "Silver nanoparticles: mechanism of antimicrobial action, synthesis, medical applications, and toxicity effects", International Nano Letters, 2012, 2:32, pp. 1-10.
U.S. Appl. No. 14/861,562, filed Sep. 22, 2015, Office Action dated Dec. 7, 2016.
U.S. Appl. No. 14/861,243, filed Sep. 22, 2015, Final Office Action dated Jan. 27, 2017.
U.S. Appl. No. 15/415,562, filed Jan. 25, 2017, Niedermeyer.
Jacobson, "These six diseases should worry you more than Ebola", Inside Energy Oct. 2014; [online] retrieved on Jan. 29, 2017 from http://www.pbs.org/newshour/updates/six-diseases-actually-worry/; 10 pages.
Pal et al., "Does the Antibacterial Activity of Silver Nanoparticles Depend on the Shape of the Nanoparticle?", Applied and Environmental Microbiology, 2007; 73(6): 1712-1720.
Rawashdeh et al., "Antibacterial Mechanisms of Metallic Nanoparticles: A Review", Dynamic Biochemistry, Process Biotechnology and Molecular Biology 2009 pp. 12-20.
Sahu et al., "Flower Shaped Silver Nanostructures: An Efficient Bacteria Exterminator", A Search for Antibacterial Agents; Chapter 2; [online] retrieved from: http://www.intechopen.com/books/a-search-for-antibacterial-agents; 2007; 73(6): 1712-1720.
U.S. Appl. No. 15/088,863, filed Apr. 1, 2016, Office Action dated Feb. 3, 2017.
U.S. Appl. No. 13/175,708, filed Jul. 1, 2011, Office Action dated Feb. 10, 2017.
U.S. Appl. No. 14/861,442, filed Sep. 22, 2015, Final Office Action dated Feb. 22, 2017.
Barcikowski et al., "Generation of nanoparticle colloids by picosecond and femtosecond laser ablations in liquid flow", Appl. Phys. Lett. 91, 083113 (2007).
Jana et al., "Seeding Growth for Size Control of 5-40 nm Diameter Gold Nanoparticles", Langmuir 2001, 17, 6782-6786.
Mafunéet al., "Formation of Stable Platinum Nanoparticles by Laser Ablation in Water", J. Phys. Chem. B 2003, 107, 4218-4223.
Phuoc et al, "Synthesis of Ag-deoionized water nanofluids using multi-beam laser ablation in fluids", Optics and Lasers in Engineering 45 (2007) 1099-1106.

(56) References Cited

OTHER PUBLICATIONS

Riabinina et al., "Influence of pressure on the Pt nanoparticle growth modes during pulsed laser ablation", Journal of Applied Physics 108, 034322 (2010, published online Aug. 12, 2010).
Sylvestre et al., "Surface Chemistry of Gold Nanoparticles Produced by Laser Ablation in Aqueous Media", J Phys. Chem. B 2004, 108, 16864-16869.
Sweeney et al., "Rapid Purification and Size Separation of Gold Nanoparticles via Diafiltration", J. Am. Chem. Soc. 2006, 128, 3190-3197 (Published on web Feb. 18, 2006).
U.S. Appl. No. 14/298,594, filed Jun. 6, 2014, Office Action dated Mar. 21, 2017.
Badawy et al., "Surface Charge-Dependent Toxicity of Silver Nanoparticles", Environ. Sci. Technol. 2011, 45, 283-287.
U.S. Appl. No. 14/861,243, filed Sep. 22, 2015, Office Action dated Mar. 9, 2016.
U.S. Appl. No. 14/298,594, filed Jun. 6, 2014, Neidermeyer.
U.S. Appl. No. 14/861,243, filed Sep. 22, 2015, Neidermeyer.
U.S. Appl. No. 14/861,318, filed Sep. 22, 2015, Neidermeyer.
U.S. Appl. No. 14/861,442, filed Sep. 22, 2015, Neidermeyer.
U.S. Appl. No. 14/861,500, filed Sep. 22, 2015, Neidermeyer.
U.S. Appl. No. 14/861,562, filed Sep. 22, 2015, Neidermeyer.
Chien et al., "Synthesis of nanoparticles: sunlight formation of gold nanodecahedra for ultra-sensitive lean-ion detection", Green Chem., vol. 13, pp. 1162-1166, May 2011.
International Search Report for PCT App. No. PCT/US2015/051642 dated Dec. 14, 2015.
International Search Report for PCT App. No. PCT/US2015/051638 dated Dec. 17, 2015.
International Search Report for PCT App. No. PCT/US2015/051640 dated Dec. 17, 2015.
International Search Report for PCT App. No. PCT/US2015/051643 dated Dec. 17, 2015.
International Search Report for PCT App. No. PCT/US2015/051649 dated Dec. 17, 2015.
International Search Report for PCT App. No. PCT/US2015/051646 dated Dec. 18, 2015.
Liu et al., "A novel coral-like porous SnO2 hollow architecture: biomimetic swallowing growth mechanism and enhanced photovoltaic property for dye-sensitized solar cell application", Chem. Commun., vol. 46, pp. 472-474, 2010.
Office Action, Jul. 1, 2011, Office Action dated May 30, 2014.
Final Office Action, Jul. 1, 2011, Final Office Action dated Nov. 13, 2014.
Office Action, Jul. 1, 2011, Office Action dated Jul. 6, 2015.

* cited by examiner

NANOPARTICLE TREATED FABRICS, FIBERS, FILAMENTS, AND YARNS AND RELATED METHODS

CROSS-REFERENCE TO RELATED APPLICATIONS

This application claims the benefit of U.S. Provisional Patent Application No. 62/054,182, filed Sep. 23, 2014, the disclosure of which is incorporated herein in its entirety.

BACKGROUND

1. Field of the Invention

Disclosed herein are nanoparticle treated fibrous articles, such as fabrics, fibers, filaments, and yarns, compositions and methods for making nanoparticle treated fibrous articles, and methods of using nanoparticle treated fibrous articles.

2. Relevant Technology

Utilization of various nanoparticle materials into and/or onto fabrics has been used in an attempt to impart characteristic advantages of a given nanoparticle to a given fabric. The term "nanoparticle" often refers to particles of any shape having a largest dimension of less than 100 nm. By way of example, silver (Ag) nanoparticles have been applied to fabrics to provide antimicrobial, antibacterial, or other related properties.

There are several notable problems with existing nanoparticle treated fabrics. For example, without a mechanism for substantially permanent immobilization of nanoparticles onto the fabric, any performance enhancement provided by the nanoparticles is quickly lost. Conversely, if a completely permanent mechanism for nanoparticle immobilization or tethering is used, the characteristics of the nanoparticles can be altered by such immobilization and their efficacy is limited as the nanoparticle is unable to freely interact as it otherwise would as a suspended, non-tethered particle. In addition, covalently bonding nanoparticles to fibers and fabric surfaces is very expensive. If, instead, the nanoparticles are merely encapsulated within a polymer or other binder material, they are generally unavailable for any purpose until the binder sloughs off, wears away, or otherwise exposes the nanoparticles.

The tradeoff between maintaining desired nanoparticle activity, on the one hand, and immobilizing the nanoparticles, on the other, has led to the development of methods for permanently attaching metal nanoparticles to fabrics and using the metal nanoparticles as a source of metal cations that provide the desired effects. This is particularly true in the case of silver (Ag) nanoparticles. Examples include covalently bonding nanoparticles onto the fibers as in U.S. Pat. No. 6,607,994, utilization of electrostatic interactions between the nanoparticles and the fabric as in U.S. Pat. Pub. No. 2009/0098366, and growing silver nanoparticles on the fabric fiber surface as in U.S. Pat. Pub. No. 2011/0110999 Immobilized silver (Ag) nanoparticles can in this way produce silver ions (Ag+) more rapidly than when using silver (Ag) threads or other macro-sized silver (Ag) components, and in a significantly more controlled manner than impregnation of fabric with silver (Ag) salts.

Regardless of the specific results or efficacy of any of these prior art solutions, each ultimately relies upon the release of metal cations into the local environment in order to provide any antimicrobial efficacy. Unfortunately, such metal cations, including heavy metal cations, ultimately make their way into the larger environment with undesirable consequences because of their fundamentally and indiscriminately toxic nature.

Noticeably absent in the art is any known or proposed mechanism for applying nanoparticles onto fibers in such a way that the desired nanoparticles remain adhered to the fibers until an active transport mechanism is presented that is capable of overcoming adhesive forces holding the particles onto the fabric surface. Such releasable adhesion of the nanoparticles to the fabric fibers would allow the nanoparticles to, at the appropriate time, go into solution without relying on a mechanism of ion release to provide antimicrobial efficacy.

SUMMARY

Disclosed herein are nanoparticle treated fibrous articles, such as fabrics, fibers, filaments, and yarns having antimicrobial properties, and related methods of manufacturing and using nanoparticle treated fibrous articles.

The nanoparticle treated fibrous articles, such as fabrics, fibers, filaments, and yarns, can include metal nanoparticles affixed thereto, such as spherical-shaped nanoparticles that can remain strongly affixed to the fabric, fiber, filament, or yarn surface without covalent bonds, without ionic bonds, and without being encapsulated by a polymer or adhesive. The spherical-shaped nanoparticles resist being washed out by conventional laundering or cleaning methods that utilize one or more of water, solvents, soaps, detergents, surfactants, and mechanical agitation. Nevertheless, when nanoparticles are contacted by a microbe they can be released into the microbes (e.g., by active absorption or other transport mechanism) and then kill or denature the microbes. Non-spherical nanoparticles, such as coral-shaped nanoparticles, can be used, preferably together with spherical-shaped nanoparticles.

According to some embodiments, nanoparticles can be releasably affixed to fibrous articles such that they adhere to the fibrous articles during normal use but are nonetheless available to microbes such as viruses, bacteria, and fungi. Because neither the nanoparticles nor the combination of the nanoparticles affixed to fibrous articles demonstrate significant cation production, but silver (Ag) nanoparticles affixed to the fibers or fabrics nonetheless demonstrate substantial antimicrobial efficacy, it is postulated that the nanoparticles are releasably affixed to the fibrous articles until an active absorption or other transport mechanism, such as provided by bacteria, causes their removal. Because nanoparticles can strongly adhere to fibrous articles, such as fabrics, fibers, filaments, and yarns, without covalent bonds, ionic bonds, or physical incorporation into a polymer or adhesive, it follows that the adhesive forces that strongly affix the nanoparticles to the fibrous articles are Van der Waals forces.

A non-limiting example of a nanoparticle treated fibrous article comprises: (1) a fabric, fiber, filament, or yarn and (2) a plurality of exposed, nonionic metal nanoparticles non-covalently affixed to the fabric, fiber, filament, or yarn. An "exposed" nanoparticle is one that is not encapsulated within another substance, such as a polymer or adhesive.

A non-limiting example of method of manufacturing a nanoparticle treated fibrous article comprises: (1) applying a nanoparticle composition comprised of a liquid carrier and a plurality of non-ionic metal nanoparticles to a fibrous article, such as a fabric, fiber, filament, or yarn, and (2) removing the liquid carrier to yield a nanoparticle treated fibrous articles in which the nonionic metal nanoparticles are exposed and non-covalently affixed to the fibrous articles.

A non-limiting example of method of a method of using a nanoparticle treated fibrous article comprises: (1) providing a nanoparticle treated fibrous article composed of (a) a fabric, fiber, filament, or yarn and (b) a plurality of exposed, nonionic metal nanoparticles non-covalently affixed to the fabric, fiber, filament, or yarn; (2) exposing the nanoparticle treated fibrous article to microbes; (3) the microbes selectively removing a portion of the exposed, nonionic metal nanoparticles from the fibrous article; and (4) the metal nanoparticles killing or denaturing the microbes.

In some embodiments, a nanoparticle treated material exhibits anti-odor properties. For example, some embodiments include a plurality of silver nanoparticles providing anti-microbial functionality (which reduces or eliminates microbial production of odor causing molecules) and a plurality of gold nanoparticles providing an additional, independent source of anti-odor functionality (e.g., by catalyzing the disruption or breakdown of amines, sulfides, organic molecules, and other odorous molecules).

In some embodiments, a nanoparticle treated material exhibits improved durability and colorfast properties. For example, some embodiments include a plurality of nanoparticles (e.g., gold nanoparticles) configured to induce a phase shift (e.g., toward the red end of the spectrum) of ultraviolet (UV) light (e.g., from sunlight) incident upon the treated material. The associated protection from ultraviolet light can beneficially improve the strength, durability, and colorfastness of the nanoparticle treated material.

In some embodiments, a nanoparticle treated material exhibits improved drying/moisture removal properties. For example, the nanoparticles of a nanoparticle treated material can provide an increased surface area for drying and/or can alter the emissivity of the treated material, thereby leading to greater removal of moisture from the treated material. Increasing emissivity can also yield a fabric or material that radiates or loses heat more quickly and feels cooler to the touch.

In some embodiments, a nanoparticle treated material exhibits radiation protection properties. For example, some embodiments include a plurality of nanoparticles (e.g., beryllium and/or gold) configured to absorb harmful radiation (e.g., alpha particles, beta particles, and/or gamma radiation), thereby reducing or eliminating an amount of radiation passing through the nanoparticle treated material.

In some embodiments, a nanoparticle treated material decreases or eliminates visibility to radar, infrared, and/or other detection methods. For example, some embodiments include a plurality of nanoparticles (e.g., cobalt nanoparticles) configured to absorb radar and/or other detection signals, thereby rendering the nanoparticle treated material invisible or less visible to detection.

In some embodiments, a nanoparticle treated material is formed as an electrically conductive material. For example, a plurality of conductive metal nanoparticles can be embedded within a fibrous article to provide the fibrous article with electrically conductive properties. The conductive properties can be tuned by adjusting the type and composition of the nanoparticles used, the concentration of the nanoparticles, and/or the distribution of nanoparticles throughout the fibrous article, for example. In one embodiment, a conductive fibrous article can be used in applications for detecting a break in a fiber and/or the level of breakage in a collection of fibers based on changes in conductivity of the material.

In some embodiments, a plurality of nanoparticles can be added to a masterbatch prior to processing of the masterbatch into fibers, fabrics, upholsteries, yarns, filaments, etc. (e.g., for polyesters, nylons, acrylics, and other synthetic fabrics). In such embodiments, the nanoparticles added to the masterbatch can be embedded in the resulting fabric. In some embodiments, the nanoparticles may be added to the masterbatch by mixing the nanoparticles in an ethylene glycol carrier or similar carrier (e.g., other alcohols and particularly other diols), and adding the resulting solution to the masterbatch. The resulting solution can have a concentration of nanoparticles with a lower bound of about 1 ppm, 3 ppm, 5 ppm, 10 ppm, 15 ppm, or 25 ppm, and an upper bound of about 50 ppm, 100 ppm, 200 ppm, 300 ppm, 400 ppm, or 500 ppm, or may have a concentration within a range of any of the foregoing upper and lower bounds, for example.

These and other advantages and features of the invention will be set forth in part in the description which follows, and in part will become apparent to those skilled in the art upon examination of the following or may be learned by practice of the invention.

DETAILED DESCRIPTION OF THE PREFERRED EMBODIMENTS

Fibrous articles, such as fabrics, fibers, filaments, and yarns, can be treated with nonionic metal nanoparticles in order to impart antimicrobial properties and/or other desired attributes such as heat transfer properties. Any known fabric, fiber, filament, or yarn can be treated with nonionic metal nanoparticles, such as those made from natural or synthetic materials.

According to some embodiments, a nanoparticle treated fibrous article comprises (1) a fabric, fiber, filament, or yarn and (2) a plurality of exposed, nonionic metal nanoparticles non-covalently affixed to the fabric, fiber, filament, or yarn. An "exposed" nanoparticle is one that is not encapsulated within another substance, such as a polymer or adhesive. The fibrous articles may comprise any known fibrous material, such as organic fibers. Examples include natural fibers (e.g., a wide variety of plant fibers or even animal derived fibers) and synthetic fibers (e.g., made from a wide variety of synthetic polymers known in the art).

Nonionic metal nanoparticles can be non-covalently affixed to fibrous articles by Van der Waals forces and can remain affixed to the fibrous article when exposed to water, soaps, surfactants, and solvents but selectively removed when contacted by a microbe such as a virus, bacterium or fungus. In some embodiments, spherical-shaped metal nanoparticles can be strongly affixed to fibrous article surfaces by Van der Waals forces. Similarly, Van der Waals forces can also act to adhere coral-shaped nanoparticles to fibrous article surfaces although perhaps not as strongly as spherical-shaped nanoparticles.

According to some embodiments, a nanoparticle treated fibrous article comprises (1) a fabric, fiber, filament, or yarn and (2) a plurality of embedded, nonionic metal nanoparticles. For example, the metal nanoparticles can be added to a masterbatch prior to processing of the masterbatch into a fibrous article.

Nanoparticle Configurations

Nanoparticles that have been found to be particularly useful in treating fibrous articles, such as fabrics, fibers, filaments, and yarns, include spherical-shaped metal nanoparticles, particularly spherical nanoparticles having diameters of about 40 nm or less, and especially spherical nanoparticles having a narrow particle size distribution. Examples of spherical-shaped metal nanoparticles and methods and systems for manufacturing essentially spherical nanoparticles having controlled particle sizes and/or narrow particle size distributions are described in U.S. Patent Publication No. 2013/0001833 (the "Niedermeyer Publication"), which is incorporated herein by reference.

Figure 1:
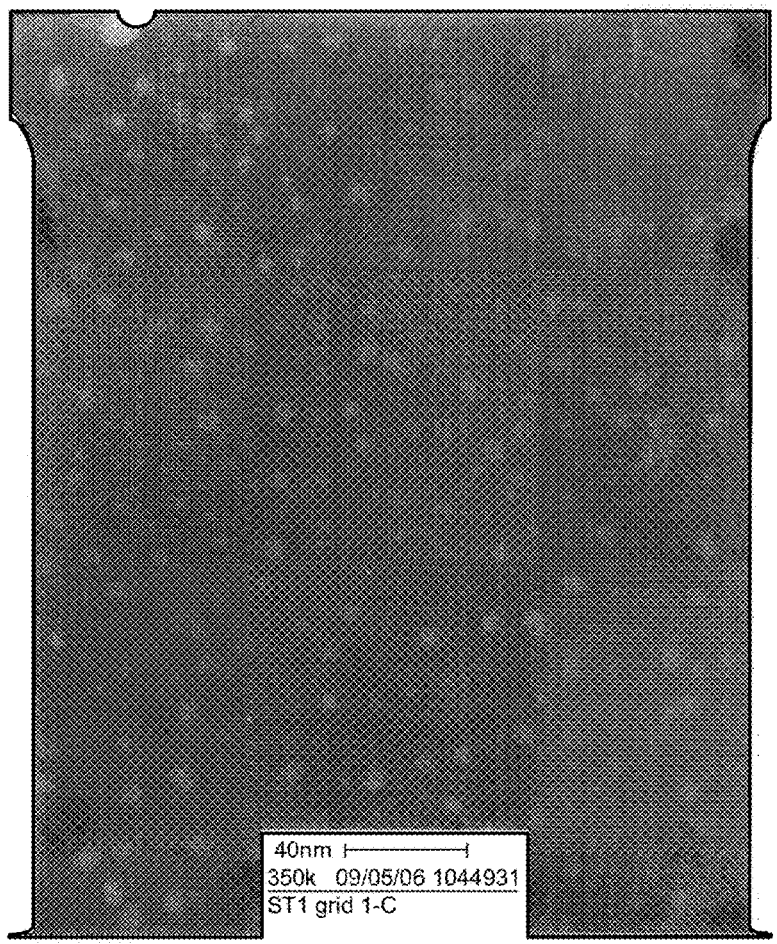
FIG. 1 is a transmission electron microscope image (TEM) of exemplary spherical-shaped metal nanoparticles having substantially uniform size and narrow particle size distribution for use in treating fibrous articles.
Figure 2A:
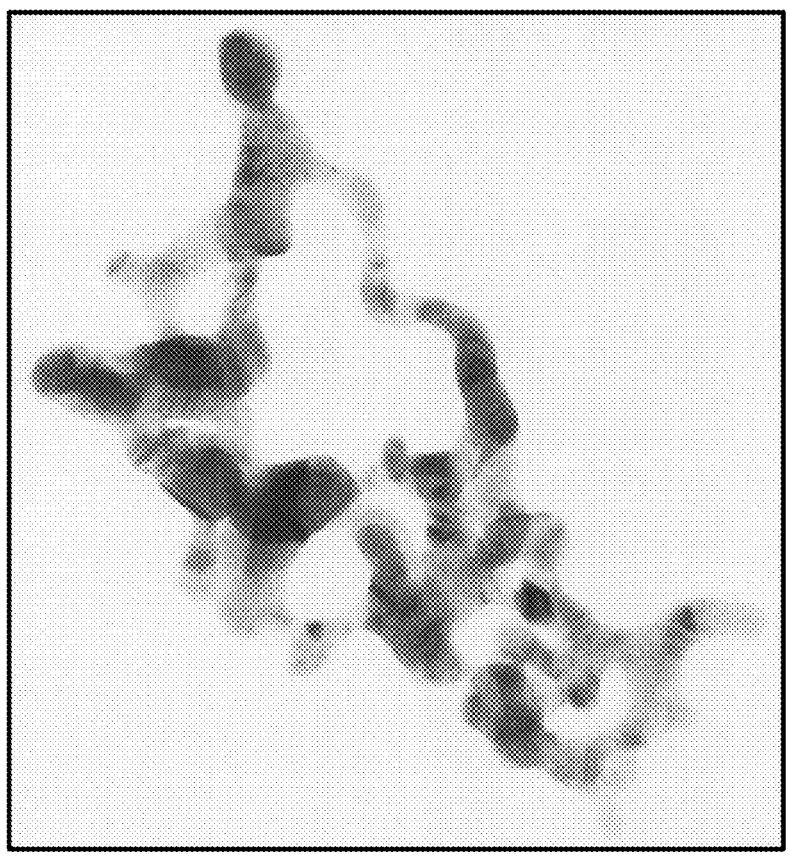
FIGS. 2A-2E are transmission electron microscope images (TEMs) of exemplary coral-shaped metal nanoparticles for use in treating fibrous articles.
Figure 2B:
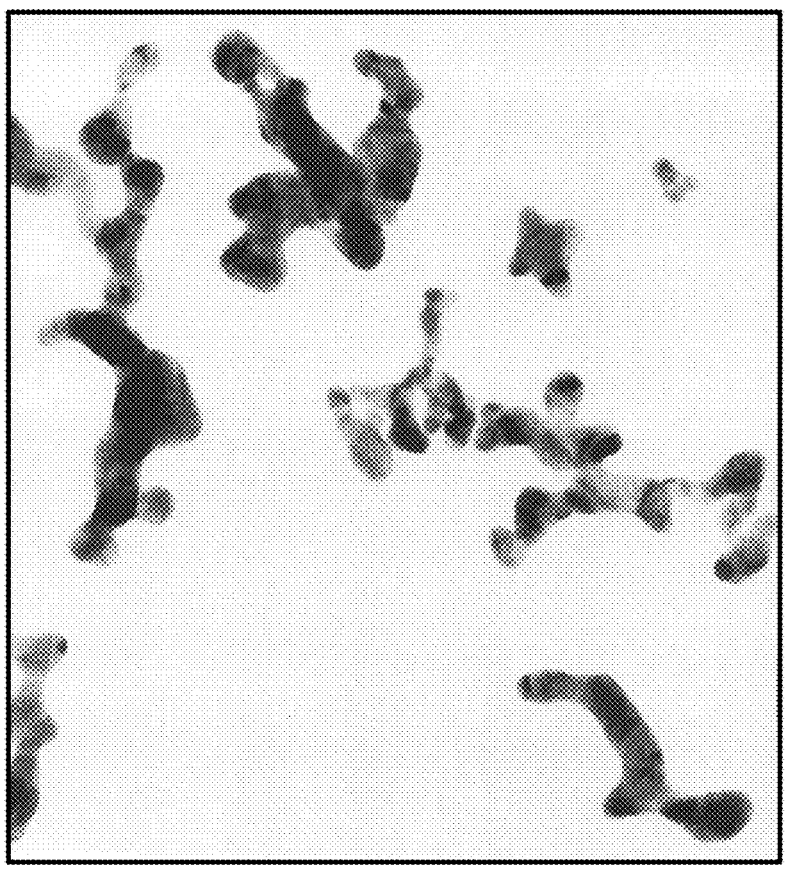
Figure 2C:
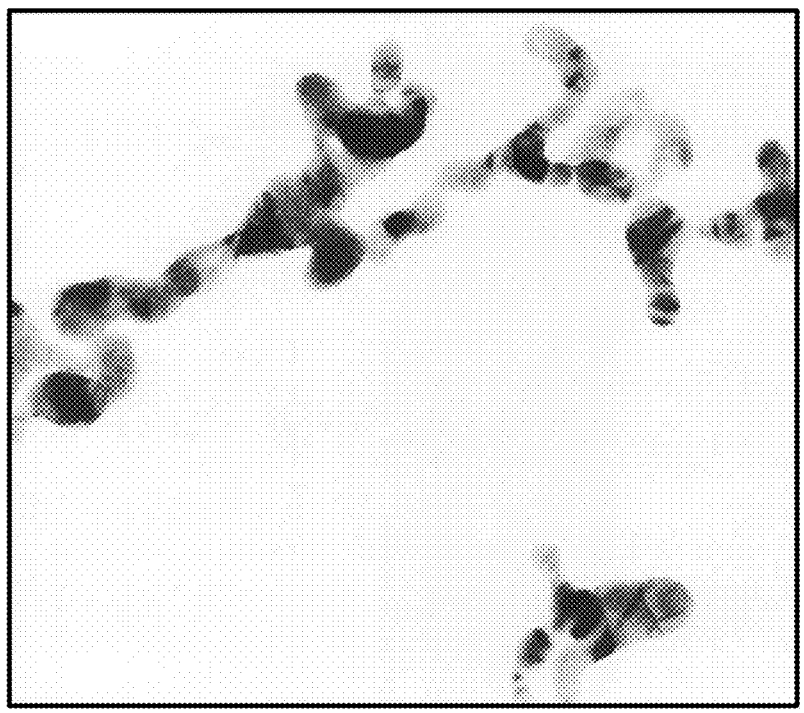
Figure 2D:
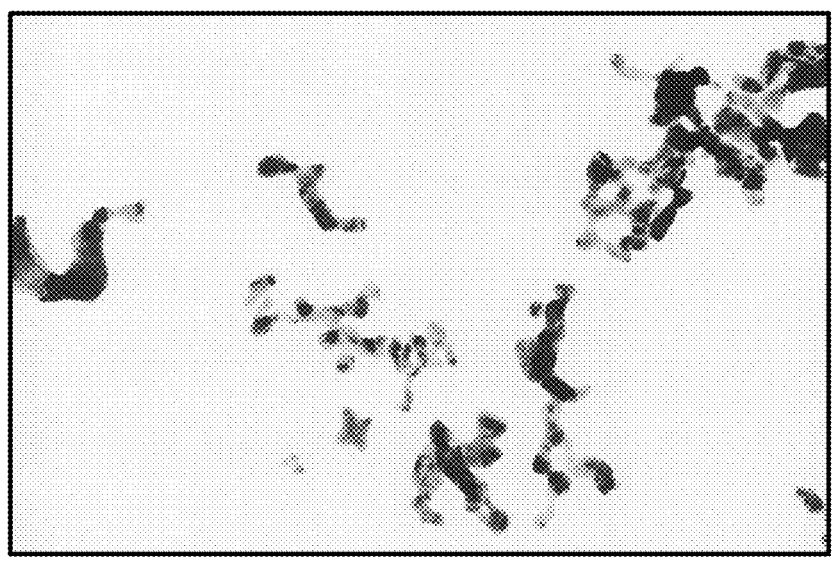
Figure 2E:
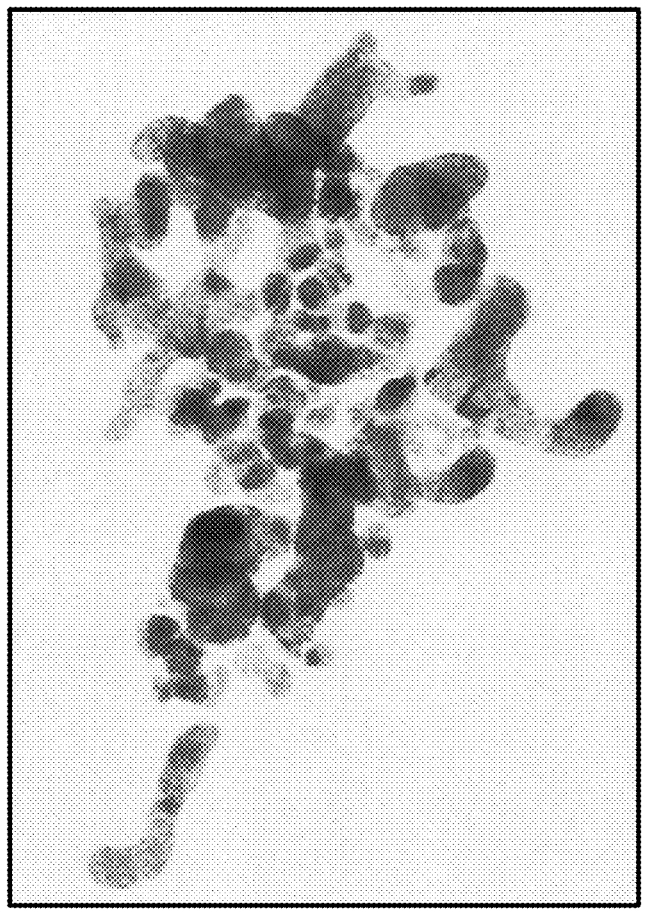

FIG. 1 is a transmission electron microscope image (TEM) of exemplary spherical-shaped metal nanoparticles made using the methods and systems of the Niedermeyer Publication. The illustrated nanoparticles are spherical-shaped silver (Ag) nanoparticles of substantially uniform size, with a mean diameter of about 10 nm and a narrow particle size distribution.

According to some embodiments, the spherical nanoparticles can have a solid core rather than being hollow, as is the case with conventional metal nanoparticles, which are usually formed on the surfaces of non-metallic seed nanoparticles (e.g., silica), which are thereafter removed to yield hollow nanospheres. Providing solid rather than hollow nanoparticles enhances their ability to be non-covalently and nonionically affixed to a fibrous article surface.

According to some embodiments, spherical-shaped metal nanoparticles include only internal angles and are free of angled edges or external bond angles, both of which can promote ionization and accumulation of point charges. Such nanoparticles can exhibit a high $\xi$-potential, which permits the spherical nanoparticles to remain dispersed within a polar solvent without a surfactant, which is a surprising and expected result. In contrast, when point charges are formed, electrostatic forces will then dominate the interaction between the nanoparticle and the fibrous article surface. Once electrostatic forces come into play, the orientation of the nanoparticle relative to the fibrous article surface will be wholly determined by those electrostatic forces. Once these electrostatic forces are neutralized, whether by surface chemistry, surfactants (detergents), static electrical charges or other external forces, the adhesive forces holding the particle to the fibrous article surface will be lost or even reversed to create a repulsive force and the interaction between the nanoparticle and the fibrous article surface will be lost.

In addition to spherical-shaped metal nanoparticles, it may be desirable to use coral-shaped nanoparticles having controlled particle sizes and/or narrow particle size distributions, such as those described in the U.S. Provisional Application No. 62/054,126, filed Sep. 23, 2104, in the name of William Niedermeyer (the "Niedermeyer Application"), and which is incorporated herein by reference.

FIGS. 2A-2E are transmission electron microscope images (TEMs) of exemplary coral-shaped metal nanoparticles made using the methods and systems of the Niedermeyer Application. Coral-shaped metal nanoparticles can have a non-uniform cross section and a globular structure formed by multiple, non-linear strands joined together without right angles. Similar to spherical nanoparticles, coral-shaped nanoparticles with no external bond angles or edges can also exhibit a high $\xi$-potential, which is a surprising and expected result. Coral-shaped nanoparticles can also be affixed to fabrics, fibers, filaments, and yarns by Van der Waals forces similar to spherical-shaped nanoparticles but often not as strongly, and can impart desired properties to fabrics, fibers, filaments, and yarns. In addition, coral-shaped nanoparticles can assist and/or augment spherical-shaped nanoparticles in becoming uniformly affixed to the fabric, fiber, filament, or yarn surface.

The nonionic metal nanoparticles may comprise any desired metal, mixture of metals, or metal alloy, including at least one of silver, gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, or alloys thereof.

According to some embodiments, nonionic metal nanoparticles useful for making nanoparticle treated fibrous articles, such as fabrics, fibers, filaments, and yarns, comprise spherical-shaped nanoparticles, preferably spherical metal nanoparticles having a solid core. In some embodiments, spherical-shaped metal nanoparticles can have a diameter of about 40 nm or less, about 35 nm or less, about 30 nm or less, about 25 nm or less, about 20 nm or less, about 15 nm or less, about 10 nm or less, about 7.5 nm or less, or about 5 nm or less. In some embodiments, spherical-shaped nanoparticles can have a particle size distribution such that at least 99% of the nanoparticles have a diameter within 30% of the mean diameter of the nanoparticles, or within 20% of the mean diameter, or within 10% of the mean diameter. In some embodiments, spherical-shaped nanoparticles can have a mean particle size and at least 99% of the nanoparticles have a particle size that is within ±3 nm of the mean diameter, ±2 nm of the mean diameter, or ±1 nm of the mean diameter. In some embodiments, spherical-shaped nanoparticles can have a $\xi$-potential of at least 10 mV, preferably at least about 15 mV, more preferably at least about 20 mV, even more preferably at least about 25 mV, and most preferably at least about 30 mV.

According to some embodiments, the nanoparticles may comprise coral-shaped nanoparticles, e.g., particles that have a non-uniform cross section and a globular structure formed by multiple, non-linear strands joined together without right angles. Coral-shaped nanoparticles can have lengths ranging from about 15 nm to about 100 nm, or about 25 nm to about 95 nm, or about 40 nm to about 90 nm, or about 60 nm to about 85 nm, or about 70 nm to about 80 nm. Coral-shaped nanoparticles can have a particle size distribution such that at least 99% of the nanoparticles have a length within 30% of the mean length, or within 20% of the mean length, or within 10% of the mean length. In some embodiments, coral-shaped nanoparticles can have a $\xi$-potential of at least 10 mV, preferably at least about 15 mV, more preferably at least about 20 mV, even more preferably at least about 25 mV, and most preferably at least about 30 mV.

In some embodiments, the nanoparticle treated fibrous article may include both spherical-shaped and coral-shaped nanoparticles (e.g., the spherical-shaped nanoparticles may comprise silver nanoparticles and the coral-shaped nanoparticles may comprise gold nanoparticles). According to one embodiment, spherical-shaped nanoparticles consist essentially or entirely of silver (Ag) nanoparticles. In the case where coral-shaped nanoparticles are used, they may consist essentially or entirely of gold (AU) nanoparticles. In some embodiments, spherical-shaped nanoparticles can comprise an alloy or mixture of silver and gold.

The nanoparticle composition may include only spherical-shaped metal nanoparticles, only coral-shaped metal nanoparticles, or both spherical-shaped and coral-shaped metal nanoparticles. In some cases, the spherical-shaped metal nanoparticles are more strongly affixed to the fibrous article than the coral-shaped metal nanoparticles. Nevertheless, the coral-shaped metal nanoparticles may assist in affixing the spherical-shaped metal nanoparticles to the fibrous article. In some embodiments, the mass ratio of spherical-shaped nanoparticles to coral-shaped nanoparticles in for treatment onto a fabric or fiber can be in a range of about 1:1 to about 50:1, or about 2.5:1 to about 25:1, or about 5:1 to about 20:1, or about 7.5:1 to about 15:1, or about 9:1 to about 11:1, or about 10:1. The particle number ratio of spherical-shaped nanoparticles to coral-shaped nanoparticles in for treatment onto a fabric or fiber can be in a range of about 10:1 to about 500:1, or about 25:1 to about 250:1, or about 50:1 to about 200:1, or about 75:1 to about 150:1, or about 90:1 to about 110:1, or about 100:1.

Releasable Affixation to Fibrous Articles

An advantage of spherical or essentially spherical nanoparticles is that they can approach a fabric, fiber, filament, or yarn surface without localized point charge forces. This allows the nanoparticle to come within the range of Van der Waals forces, with the overall force increasing inversely relative to the distance between the nanoparticle and the fibrous article surface. Empirical tests verify the strength of the adhesive forces between the nanoparticles and the fibrous article surface, with tests demonstrating that the nanoparticles remain affixed to the fibrous article surface through routine uses, including applied frictional forces, multiple wash cycles using standard fabric detergents, and heat from a clothes dryer (in excess of 50 wash and drying cycles).

By way of example, a fabric containing spherical-shaped nanoparticles affixed to a surface was subjected to 50 wash and dry cycles in a conventional washer and dryer. No ionic silver (Ag$^+$) was detected in the wash water. Because the spherical-shaped nanoparticles were firmly affixed to the fabric without covalent bonds and ionic bonds and without being embedded within the fabric or a within a coating matrix, yet able to withstand being removed when washed and heat dries, it is postulated that they are nonionic, have no point charges, and are affixed to the fabric, fiber, filament, or yarn by Van der Waals forces.

Figure 3:
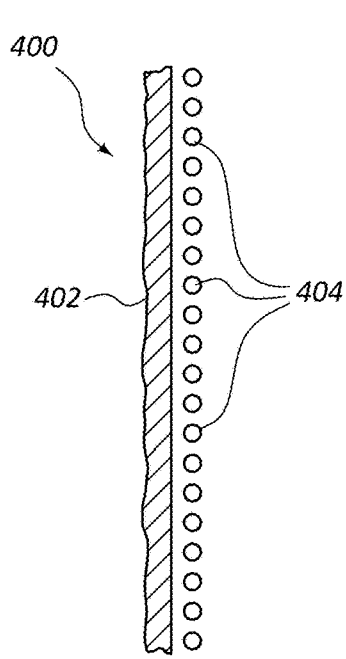
FIG. 3 schematically illustrates a fibrous article surface and a plurality of spherical-shaped nanoparticles affixed thereto.

FIG. 3 schematically illustrates a nanotreated fabric, fiber, filament, or yarn 400, which includes a fibrous article surface 402 and a plurality of spherical-shaped nanoparticles 404 affixed thereto. The spherical-shaped nanoparticles 404 are preferentially affixed to the fibrous article surface 402 in a substantially uniform concentration or distribution in order to provide similar properties throughout the fibrous article.

According to some embodiments, the concentration of nanoparticles is generally about 0.1 mg to about 1 mg per yard of fabric.

Figure 4:
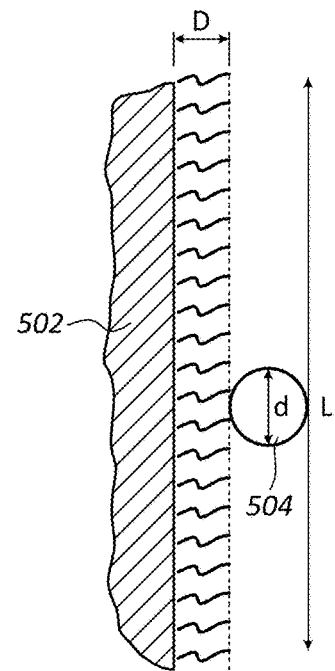
FIG. 4 is a theoretical model showing a spherical-shaped metal nanoparticle strongly affixed to a fibrous article surface without covelent or ionic bonds.

FIG. 4 is a theoretical model showing a spherical-shaped metal nanoparticle strongly affixed to a fibrous article surface 502 without covelent or ionic bonds. It is postulated that when an exposed, nonionic, spherical-shaped metal nanoparticle 504 is within a distance D (e.g., about 35 nm for a silver (Ag) nanoparticle) of fibrous article surface 502, the surface 502 "sees" the nanoparticle as a flat elongated surface rather than a sphere. If the spherical-shaped metal nanoparticle 504 interacted with the fibrous article surface 502 as a sphere rather than a flat surface, only the few atoms of the spherical nanoparticle nearest the fibrous article surface surface 502 would be attracted by Van der Waals forces, and the forces acting on the other atoms would drop off quickly. In that case, the relatively high mass of the nanoparticle would overcome and overwhelm the relatively small Van der Waals forces applied to the closest atoms and the nanoparticle would easily fall off. However, because nanoparticle 504 is instead tightly affixed to fibrous article surface 502, nanoparticle 504 apparently interacts with surface 502 in a way so as to be "seen" as an enlarged flat surface. The Van der Waals forces act with essentially equal attractive force to the entire flat surface, which greatly enhances the magnitude of the attractive Van der Waals forces acting to affix nanoparticle 504, and nanoparticle 504 is instead tightly affixed to fibrous article surface 502. This has been empirically shown to be true. Moreover, mathematical calculations predict that solid, spherical metal nanoparticles can behave and interact with a surface in the manner depicted in FIG. 4.

Active Transport Mechanisms

The nanoparticle treated fibrous article can be coated with a generally even distribution of nanoparticles, which will remain on the fibrous article surface until an active absorption or other transport mechanism is presented that is capable of overcoming the attractive forces. Active absorption or other transport mechanism results when a microbe, such as a virus, bacterium or fungus, comes into contact with the nanoparticle treated fibrous article such that the microbe physically contacts at least one nanoparticle. Because an individual nanoparticle is so much smaller than the microbe, particularly bacteria and fungi, microbes actively absorb materials from their environment, and individual nanoparticles are not covalently bonded to or physically incorporated into the fibrous structure of the article, the nanoparticles can be actively absorbed or transported from the surface of the fibrous article into the microbe where appropriately chosen particles can then kill or inactivate the microbe.

Although nanoparticles tightly held to a fibrous article surface by Van der Waals forces have been shown to withstand typical environmental forces and will remain on the fibrous article surface through normal activities, the attractive forces between the nanoparticles and fibrous article surface are not permanent and insurmountable, such as in a covalent bond or where the particles are bound within the structure of the fabric or a matrix of a coating. As a result, the adhesive forces affixing the nanoparticles can be overcome and the nanoparticles can be released when the particles interact with other surfaces that present an active transport mechanism, such as bacteria, fungi, or even viruses. Such microbes have different cellular compositions and cell wall functions than those typical of human and mammalian cells, such as hair and skin that typically would come in contact with a fabric, fiber, filament, or yarn.

Figure 5:
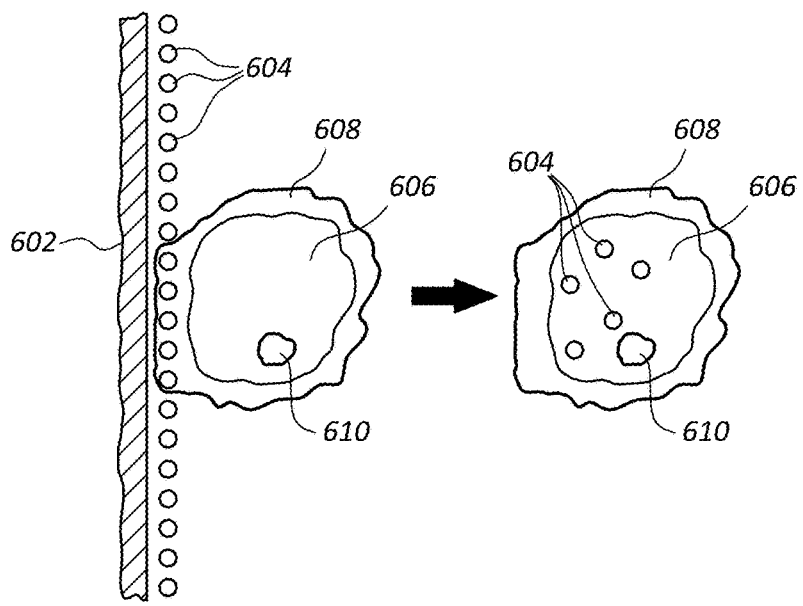
FIG. 5 schematically illustrates a microbe approaching a fibrous article surface and removing a portion of the spherical-shaped nanoparticles.
Figure 6:
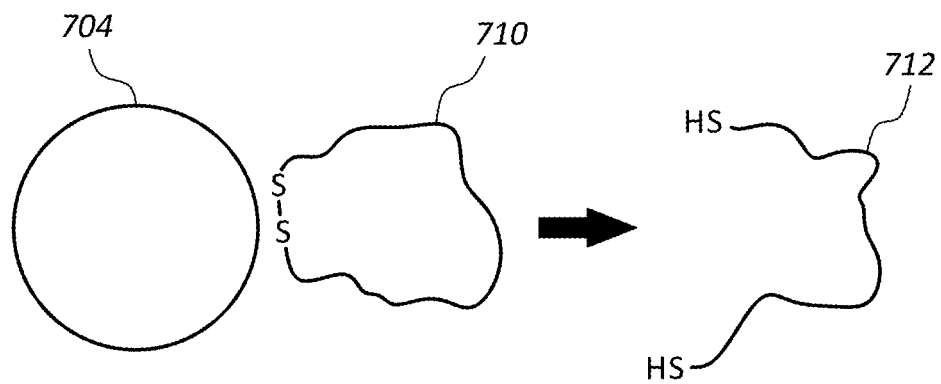
FIG. 6 schematically illustrates a microbe protein with disulfide bonds being catalytically denatured by an adjacent spherical-shaped nanoparticle.
Figure 7:
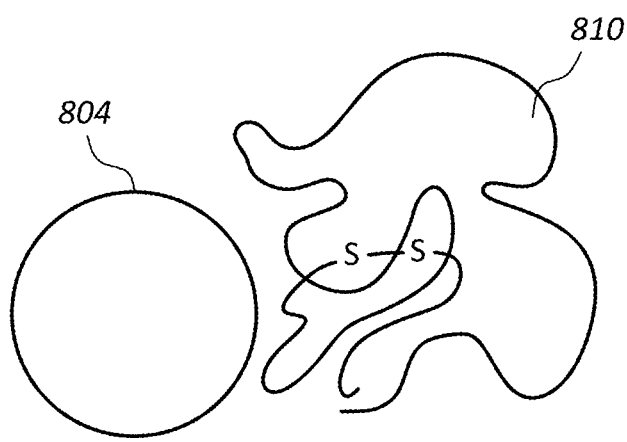
FIG. 7 schematically illustrates a mammalian protein with disulfide bonds that are shielded so as to resist being catalytically denatured by an adjacent spherical-shaped nanoparticle.

FIG. 5 schematically illustrates a proposed model by which a microbe 608 approaching a fibrous article surface 602 with spherical-shaped nanoparticles 604 affixed thereto can remove one or more of the spherical-shaped nanoparticles 604 from fibrous article surface 602, such as by active absorption or other transport mechanism. The removed nanoparticles 604 can freely move throughout the interior 606 of microbe 608 and come into contact with one or more vital proteins or enzymes 610 that, if denatured, will kill or disable the microbe.

Antimicrobial Activity

One way that nanoparticles may kill or denature a microbe is by catalyzing the cleavage of disulfide (S—S) bonds within a vital protein or enzyme. FIG. 6 schematically illustrates a microbe protein or enzyme 710 with disulfide bonds being catalytically denatured by an adjacent spherical-shaped nanoparticle 704 to yield denatured protein or enzyme 712. In the case of bacteria or fungi, the cleavage of disulfide bonds and/or cleavage of other chemical bonds of vital proteins or enzymes may occur within the cell interior, thereby killing the microbe in this manner. Such catalytic cleavage of disulfide (S—S) bonds is facilitated by the generally simple protein structures of microbes, in which many vital disulfide bonds are exposed and readily cleaved by catalysis.

Another mechanism by which metal (e.g., silver) nanoparticles can kill microbes is through the production of active oxygen species, such as peroxides, which can oxidatively cleave protein bonds, including but not limited to amide bonds.

In the case of viruses, spherical-shaped and coral-shaped metal nanoparticles can deactivate viruses by attaching to glycoproteins and/or catalyzing protein denaturing reactions in the protein coat so that the virus is no longer able to attach to a host cell and/or inject genetic material into the host cell. Because very small nanoparticles can pass through a virus, denaturing of the protein coat may occur within the interior of the virus. A virus that is rendered unable to attach to a host cell and/or inject genetic material into the host cell is essentially inactive and no longer pathogenic.

Notwithstanding the lethal nature of nonionic metal nanoparticles relative to microbes, they can be relatively harmless to humans, mammals, and healthy mammalian cells, which contain much more complex protein structures compared to simple microbes in which most or all vital disulfide bonds are shielded by other, more stable regions of the protein. FIG. 7 schematically illustrates a mammalian protein 810 with disulfide (S—S) bonds that are shielded so as to resist being catalytically denatured by an adjacent spherical-shaped nanoparticle 804. In many cases the nonionic nanoparticles do not interact with or attach to human or mammalian cells, remain in and follow fluid flow, do not cross barriers, remain in the vascular system, and can be quickly and safely expelled through the urine without damaging kidneys or other cells.

In the particular case of silver (Ag) nanoparticles, the interaction of the silver (Ag) nanoparticle(s) within a microbe has been demonstrated to be particularly lethal without the need to rely on the production of silver ions ($Ag^+$) to provide the desired antimicrobial effects, as is typically the case with conventional colloidal silver treatments of fabrics. In addition, the ability of affixed metal nanoparticles to be preferentially released directly into microbial cells minimized the release of potentially toxic metal cations into the local and larger environment. The ability of silver (Ag) nanoparticles to be affixed to fibrous articles while providing effective microbial control without any significant release of toxic silver ions ($Ag^+$) into the surrounding environment is a substantial advancement in the art.

The size of the particles can be selected to target and kill specific types of microbes. For example, nanoparticle may be size optimized to selectively target and kill certain microbes. By way of example, nanoparticles having a diameter of less than about 8 nm (e.g., about 1-7 nm, or about 2-6.5 nm, or about 3-6 nm) have been found to be effective in killing viruses, nanoparticles having a diameter of about 3-14 nm (e.g., about 5-13 nm, or about 7-12 nm, or about 8-10 nm) have been found to be effective in killing bacteria, and nanoparticles having a diameter of about 9-20 nm (e.g., about 10-18 nm, or about 11-16 nm, or about 12-15 nm) have been found to be effective in killing fungi. Within the foregoing ranges, there may be specific sizes of nanoparticles that are most effective in killing a particular type of virus, bacterium, or fungus. For example, sub-micron sized metal nanoparticles (e.g., gold nanoparticles having a diameter of about 0.4 nm) may be most effective in killing ebola viruses due their oddly elongated and looped configuration.

Other Exemplary Beneficial Properties

In addition to providing fibrous articles, such as fabrics, fibers, filaments, and yarns, with antimicrobial properties, which reduces or eliminates odors and kills potentially dangerous pathogens, the nanoparticles can also impart high temperature transfer properties, yielding clothing and other fibrous articles that feel cooler to the wearer. Fibrous articles treated with nonionic metal nanoparticles as disclosed herein can have improved thermodynamic heat transfer properties, such as increased convention (e.g., increased water evaporation) and increased thermal emissivity (e.g., radiation of heat). Nanoparticle treated fabrics and other fibrous articles can move heat faster to the surrounding environment than untreated fabrics. In addition, while nanoparticle treated fibrous articles as disclosed herein provide improved convection properties similar to conventional fabrics treated with colloidal silver, the increase in thermal emissivity requires, and is only provided by, spherical-shaped nanoparticles of narrow particle size distribution. This is a surprising and unexpected result.

In some embodiments, a nanoparticle treated fabric exhibits anti-odor properties. For example, some embodiments include a plurality of silver nanoparticles providing antimicrobial functionality (which reduces or eliminates microbial production of odor causing molecules) and a plurality of gold nanoparticles providing an additional, independent source of anti-odor functionality (e.g., by catalyzing the disruption of amines, sulfides, organic molecules, and other odorous molecules).

In some embodiments, a nanoparticle treated fabric exhibits improved durability and colorfast properties. For example, some embodiments include a plurality of nanoparticles (e.g., gold nanoparticles) configured to induce a phase shift (e.g., toward the red end of the spectrum) of ultraviolet light incident upon the treated fabric. The associated protection from ultraviolet light can beneficially improve the strength, durability, and color-fastness of the nanoparticle treated fabric.

In some embodiments, a nanoparticle treated fabric exhibits improved drying/moisture removal properties. For example, the nanoparticles of a nanoparticle treated fabric can provide an increased surface area for drying and/or can alter the emissivity of the treated fabric, thereby leading to greater removal of moisture from the treated fabric.

In some embodiments, a nanoparticle treated material exhibits radiation protection properties. For example, some embodiments include a plurality of nanoparticles (e.g., beryllium and/or gold) configured to absorb harmful radiation (e.g., alpha particles, beta particles, and/or gamma radiation), thereby reducing or eliminating an amount of radiation passing through the nanoparticle treated material.

In some embodiments, a nanoparticle treated material decreases or eliminates visibility to radar, infrared, and/or other detection methods. For example, some embodiments include a plurality of nanoparticles (e.g., cobalt nanoparticles) configured to absorb radar and/or other detection signals, thereby rendering the nanoparticle treated material invisible or less visible to detection.

In some embodiments, a nanoparticle treated material is formed as an electrically conductive material. For example, a plurality of conductive metal nanoparticles can be embedded within a fibrous article to provide the fibrous article with electrically conductive properties. The conductive properties can be tuned by adjusting the type and composition of the nanoparticles used, the concentration of the nanoparticles, and/or the distribution of nanoparticles throughout the fibrous article, for example. In one embodiment, a conductive fibrous article can be used in applications for detecting a break in a fiber and/or the level of breakage in a collection of fibers based on changes in conductivity of the material.

Methods of Manufacture and Use

According to some embodiments, a method of manufacturing a nanoparticle treated fibrous article comprises: (1) applying a nanoparticle composition comprised of a liquid carrier and a plurality of nonionic metal nanoparticles to a fibrous article, such as a fabric, fiber, filament, or yarn, and (2) removing the liquid carrier to yield a nanoparticle treated fibrous article in which the nonionic metal nanoparticles are exposed and non-covalently affixed to the fibrous article. In some embodiments, at least a portion of the nonionic metal nanoparticles can be non-covalently affixed to the fibrous article by Van der Waals forces.

According to some embodiments, the liquid carrier comprises one or more of a non-polar liquid, an organic solvent, a polar liquid, or an aqueous liquid. Examples of suitable liquid carriers include water, methanol, ethanol, isopropyl alcohol, other alcohols, acetone, ketones, aldehydes, and ethyl acetate.

In some cases it may be desirable for the liquid carrier to be volatile so that when applying the nanoparticle composition to a fibrous article the volatile liquid carrier can be removed by evaporation rather than running through or past the surface being treated, which can carry the nanoparticles away and prevent adherence to the surface. According to some embodiments, the volatile liquid carrier is advantageously removed by evaporation while applying the nanoparticle composition to the fibrous article. For example, the nanoparticle composition can be applied to a fabric or other fibrous article by dry fogging. Alternatively, the nanoparticle composition can be applied by dipping, followed by fast drying of the volatile liquid in order to leave behind sufficient nanoparticle residue. The application process can be repeated to yield a fabric or other fibrous article having a desired concentration of nanoparticles.

According to some embodiments, a nanoparticle composition comprised of ethanol and spherical metal nanoparticles, and devoid of any surfactant, is applied to a fabric or other fibrous article by spraying and simultaneous evaporation of the ethanol in order to coat the fabric or other fibrous article surface with spherical metal nanoparticles, the spherical metal nanoparticles being strongly affixed by Van der Waals forces. According to another embodiment, coral-shaped metal nanoparticles can also be included in order to help carry and attach the spherical metal nanoparticles to the fabric or other fibrous article surface. After application and drying of the solvent, coral-shaped metal nanoparticles may be attached less strongly to the fibrous article compared to spherical-shaped metal nanoparticles. In some cases it may be possible to selectively remove coral-shaped nanoparticle, e.g., for reuse, while leaving spherical-shaped nanoparticles in place.

In some embodiments, a plurality of nanoparticles can be added to a masterbatch prior to processing of the masterbatch into fibers, fabrics, upholsteries, yarns, filaments, etc. (e.g., for polyesters, nylons, acrylics, and other synthetic fabrics). In such embodiments, the nanoparticles added to the masterbatch can be embedded in the resulting fabric. In some embodiments, the nanoparticles may be added to the masterbatch by mixing the nanoparticles in an ethylene glycol carrier or similar carrier (e.g., other alcohols and particularly other diols), and adding the resulting solution to the masterbatch. The resulting solution can have a concentration of nanoparticles with a lower bound of about 1 ppm, 3 ppm, 5 ppm, 10 ppm, 15 ppm, or 25 ppm, and an upper bound of about 50 ppm, 100 ppm, 200 ppm, 300 ppm, 400 ppm, or 500 ppm, or may have a concentration within a range of any of the foregoing upper and lower bounds, for example.

In some embodiments, a method of manufacture in which the nonionic metal nanoparticles are exposed and non-covalently affixed to the fibrous article can be useful for antimicrobial applications or other applications where it may be beneficial for at least some of the metal nanoparticles to be detachably affixed to the treated fibrous article, for example. In some embodiments, a method of manufacture in which at least some of the nonionic metal nanoparticles are embedded in the fibrous article (e.g., are mixed with a masterbatch prior to processing of the masterbatch) can be useful for anti-radiation, anti-radar, and/or electrically conductive fabric applications, for example. The foregoing methods of manufacture can be combined, altered, and/or adjusted to meet needs and preferences.

According to some embodiments, a method of using a nanoparticle treated fibrous article comprises: (1) providing a nanoparticle treated fibrous article, such as a nanoparticle treated fabric, fiber, filament, or yarn, as described herein; (2) exposing the nanoparticle treated fibrous article to microbes; (3) the microbes selectively removing a portion of the exposed, nonionic metal nanoparticles from the fibrous article; and (4) the metal nanoparticles killing or denaturing the microbes.

The nanoparticle treated fibrous article can be further exposed to one or more of water, soap, surfactant, or solvent; however, the metal nanoparticles can remain attached to the fibrous article except when contacted by a microbe. In the case where the metal nanoparticles comprise both spherical-shaped and coral-shaped nanoparticles, spherical-shaped metal nanoparticles can be more strongly affixed to the fibrous article surface than coral-shaped metal nanoparticles. When exposing the nanoparticle treated fibrous article to one or more of water, soap, surfactant, or solvent, the spherical-shaped metal nanoparticles can remain attached to the fabric, fiber, filament, or yarn except when contacted by a microbe, and at least a portion of the coral-shaped metal nanoparticles can be more easily removed by the one or more of water, soap, surfactant, or solvent.

EXAMPLES

Example 1

To manufacture a nanoparticle treated fabric, 1 mg/L of 25 nm spherical-shaped gold (Au) nanoparticles, 1 mg/L of 70 nm coral-shaped gold (Au) nanoparticles, and 1 mg/L of 10 nm spherical-shaped silver (Ag) nanoparticles were put into a distilled water solution for application onto polyester fabric utilizing a dry fog system.

Example 2

To manufacture a nanoparticle treated fabric, 1 mg/L of 25 nm spherical-shaped gold (Au) nanoparticles, 1 mg/L of 70 nm coral-shaped gold (Au) nanoparticles, and 2 mg/L of 10 nm spherical-shaped silver (Ag) nanoparticles were put into a distilled water solution for application onto cotton fabric utilizing a dry fog system.

Example 3

To manufacture a nanoparticle treated fabric, 1 mg/L of 25 nm spherical-shaped gold (Au) nanoparticles, 1 mg/L of 70 nm coral-shaped gold (Au) nanoparticles, and 5 mg/L of 10 nm spherical-shaped silver (Ag) nanoparticles were put into a distilled water solution for application onto polyester fabric utilizing a dry fog system.

Example 4

To manufacture a nanoparticle treated fabric, 1 mg/L of 25 nm spherical-shaped gold (Au) nanoparticles, 1 mg/L of 70 nm coral-shaped gold (Au) nanoparticles, and 10 mg/L of 10 nm spherical-shaped silver (Ag) nanoparticles were put into a distilled water solution for application onto cotton fabric utilizing a dry fog system.

Example 5

To manufacture a nanoparticle treated fabric, 1 mg/L of 25 nm spherical-shaped gold (Au) nanoparticles, 1 mg/L of 70 nm coral-shaped gold (Au) nanoparticles, and 1 mg/L of 10 nm spherical-shaped silver (Ag) nanoparticles were put into a 5% ethanol 95% distilled water solution for application onto cotton fabric utilizing a dry fog system.

Example 6

To manufacture a nanoparticle treated fabric, 1 mg/L of 25 nm spherical-shaped gold (Au) nanoparticles, 1 mg/L of 70 nm coral-shaped gold (Au) nanoparticles, and 2 mg/L of 10 nm spherical-shaped silver (Ag) nanoparticles were put into a 5% ethanol 95% distilled water solution for application onto polyester fabric utilizing a dry fog system.

Example 7

To manufacture a nanoparticle treated fabric, 1 mg/L of 25 nm spherical-shaped gold (Au) nanoparticles, 1 mg/L of 70 nm coral-shaped gold (Au) nanoparticles, and 5 mg/L of 10 nm spherical-shaped silver (Ag) nanoparticles were put into a 5% ethanol 95% distilled water solution for application onto polyester fabric utilizing a dry fog system.

Example 8

To manufacture a nanoparticle treated fabric, 1 mg/L of 25 nm spherical-shaped gold (Au) nanoparticles, 1 mg/L of 70 nm coral-shaped gold (Au) nanoparticles, and 10 mg/L of 10 nm spherical-shaped silver (Ag) nanoparticles were put into a 5% ethanol 95% distilled water solution for application onto cotton fabric utilizing a dry fog system.

Example 9

To manufacture a nanoparticle treated fabric, 1 mg/L of 25 nm spherical-shaped gold (Au) nanoparticles, 1 mg/L of 70 nm coral-shaped gold (Au) nanoparticles, and 1 mg/L of 10 nm spherical-shaped silver (Ag) nanoparticles were put into a 95% ethanol solution for application onto cotton fabric utilizing a dry fog system.

Example 10

To manufacture a nanoparticle treated fabric, 1 mg/L of 25 nm spherical-shaped gold (Au) nanoparticles, 1 mg/L of 70 nm coral-shaped gold (Au) nanoparticles, and 2 mg/L of 10 nm spherical-shaped silver (Ag) nanoparticles were put into a 95% ethanol solution for application onto polyester fabric utilizing a dry fog system.

Example 11

To manufacture a nanoparticle treated fabric, 1 mg/L of 25 nm spherical-shaped gold (Au) nanoparticles, 1 mg/L of 70 nm coral-shaped gold (Au) nanoparticles, and 5 mg/L of 10 nm spherical-shaped silver (Ag) nanoparticles were put into a 95% ethanol solution for application onto polyester fabric utilizing a dry fog system.

Example 12

To manufacture a nanoparticle treated fabric, 1 mg/L of 25 nm spherical-shaped gold (Au) nanoparticles, 1 mg/L of 70 nm coral-shaped gold (Au) nanoparticles, and 10 mg/L of 10 nm spherical-shaped silver (Ag) nanoparticles were put into a 95% ethanol solution for application onto cotton fabric utilizing a dry fog system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A nanoparticle treated fibrous article, comprising:

a fibrous article selected from a fabric, fiber, filament, or yarn; and a plurality of exposed, nonionic, spherical-shaped metal nanoparticles free of angled edges or external bond angles, the metal nanoparticles being formed through a laser-ablation process, at least a portion of the metal nanoparticles being silver nanoparticles that provide effective microbial control without significant release of toxic silver ions, and the metal nanoparticles being non-covalently affixed to the fibrous article through Van der Waals forces, without electrostatic forces, without being embedded within a fiber, filament, or yarn of the fibrous article, and without being encapsulated within a polymer or adhesive coating, wherein the metal nanoparticles remain affixed to the fibrous article when exposed to one or more of water, soap, a surfactant, or a solvent.

2. A nanoparticle treated fibrous article as in claim 1, wherein the nonionic metal nanoparticles further comprise at least one metal selected from the group consisting of gold, platinum, palladium, rhodium, osmium, ruthenium, rhodium, rhenium, molybdenum, copper, iron, nickel, tin, beryllium, cobalt, antimony, chromium, manganese, zirconium, tin, zinc, tungsten, titanium, vanadium, lanthanum, cerium, heterogeneous mixtures thereof, and alloys thereof.

3. A nanoparticle treated fibrous article as in claim 1, wherein the nonionic metal nanoparticles have a mean diameter or length and wherein at least 99% of the metal nanoparticles have a diameter or length within 30% of the mean diameter or length.

4. A nanoparticle treated fibrous article as in claim 1, wherein the nonionic metal nanoparticles have a $\xi$-potential of at least 10 mV.

5. A nanoparticle treated fibrous article as in claim 1, wherein the nonionic metal nanoparticles have a solid core and a diameter of 40 nm or less.

6. A nanoparticle treated fibrous article as in claim 5, wherein the spherical-shaped metal nanoparticles have a mean diameter and wherein at least 99% of the spherical-shaped nanoparticles have a diameter within ±3 nm of the mean diameter.

7. A nanoparticle treated fibrous article as in claim 1, further comprising nonionic, metal, coral-shaped nanoparticles.

8. A nanoparticle treated fibrous article as in claim 7, wherein the spherical-shaped nanoparticles comprise silver nanoparticles and the coral-shaped nanoparticles comprise gold nanoparticles.

9. A nanoparticle treated fibrous article as in claim 1, wherein the nonionic metal nanoparticles non-covalently affixed to the fabric, fiber, filament, or yarn by Van der Waals forces remain affixed to the fabric, fiber, filament, or yarn when exposed to water, soaps, surfactants, and solvents but are selectively removeable when contacted by a microbe.

10. A method of manufacturing a nanoparticle treated fibrous article, comprising:
applying a nanoparticle composition comprised of a liquid carrier and a plurality of nonionic, metal nanoparticles to an outer surface of a fibrous article selected from a fabric, fiber, filament, or yarn, the metal nanoparticles being spherical-shaped and free of angled edges or external bond angles, and the nanoparticles being formed through a laser-ablation process,
wherein at least a portion of the metal nanoparticles being silver nanoparticles that provide effective microbial control without significant release of toxic silver ions; and
removing the liquid carrier to yield a nanoparticle treated fibrous article in which the nonionic, metal nanoparticles are exposed and non-covalently affixed to the fibrous article through Van der Waals forces, without electrostatic forces, and without being embedded within the fibrous article and without being encapsulated in a polymer or adhesive coating,
wherein the metal nanoparticles remain affixed to the fibrous article when exposed to one or more of water, soap, a surfactant, or a solvent.

11. A method as in claim 10, wherein the liquid carrier is volatile and wherein applying the nanoparticle composition includes removing the volatile liquid carrier by evaporation.

12. A method as in claim 10, wherein the nanoparticle composition is applied to the fibrous article by dry fogging.

13. A nanoparticle treated fibrous article formed by the method of claim 10.

14. A nanoparticle treated fibrous article as in claim 13, wherein the plurality of nonionic metal nanoparticles include beryllium nanoparticles and the fibrous article absorbs harmful radiation.

15. A nanoparticle treated fibrous article as in claim 13, wherein the plurality of nonionic metal nanoparticles include cobalt nanoparticles and the fibrous article absorbs radar.

16. A nanoparticle treated fibrous article as in claim 13, wherein the plurality of nonionic metal nanoparticles are configured to induce a phase shift of at least a portion of ultraviolet light incident upon the fibrous article.

17. A nanoparticle treated fibrous article as in claim 13, wherein the fibrous article is electrically conductive.

18. A nanoparticle treated fibrous article, comprising:
a fibrous article selected from a fabric, fiber, filament, or yarn;
a plurality of exposed, solid, nonionic, spherical-shaped silver nanoparticles free of angled edges or external bond angles, the silver nanoparticles being non-covalently affixed to the fibrous article through Van der Waals forces, without electrostatic forces, without being embedded within the fibrous article, and without being encapsulated within a polymer or adhesive coating; and
a plurality of solid, nonionic, gold nanoparticles non-covalently affixed to the fibrous article,
wherein the silver nanoparticles remain affixed to the fibrous article when exposed to one or more of water, soap, a surfactant, or a solvent, and
wherein the silver nanoparticles provides an anti-odor effect via anti-microbial activity and the gold nanoparticles provides an independent anti-odor effect via catalyzing the breakdown of odorous molecules.

19. A nanoparticle treated fibrous article as in claim 1, wherein the fibrous article, when subjected to multiple wash cycles in wash water, releases no detectable ionic silver into the wash water.

20. A method as in claim 10, further comprising subjecting the fibrous article to multiple wash cycles in wash water, the fibrous article releases no detectable ionic silver into the wash water.

* * * * *